US010392487B2

(12) United States Patent
Taylor et al.

(10) Patent No.: US 10,392,487 B2
(45) Date of Patent: Aug. 27, 2019

(54) PROCESS FOR EXTENDING THE SHELF LIFE OF GASEOUS OLEFINIC PROPELLANTS IN POLYURETHANE FOAMS

(71) Applicant: ICP Adhesives and Sealants, Inc., Norton, OH (US)

(72) Inventors: Anthony J. Taylor, Medina, OH (US); Julie L. Shoemaker, Wadsworth, OH (US); Andrew P. Shinko, Uniontown, OH (US)

(73) Assignee: ICP Adhesives and Sealants, Inc., Norton, OH (US)

(*) Notice: Subject to any disclaimer, the term of this patent is extended or adjusted under 35 U.S.C. 154(b) by 0 days.

(21) Appl. No.: 16/033,276

(22) Filed: Jul. 12, 2018

(65) Prior Publication Data

US 2019/0092920 A1 Mar. 28, 2019

Related U.S. Application Data

(62) Division of application No. 14/992,338, filed on Jan. 11, 2016, now Pat. No. 10,059,824.

(60) Provisional application No. 62/102,289, filed on Jan. 12, 2015.

(51) Int. Cl.

| *C08J 9/14* | (2006.01) |
|---|---|
| *G01N 33/44* | (2006.01) |
| *C08G 18/48* | (2006.01) |
| *C08G 18/66* | (2006.01) |
| *C08G 18/76* | (2006.01) |
| *C08G 18/16* | (2006.01) |
| *C08G 18/18* | (2006.01) |
| *C08G 18/22* | (2006.01) |
| *C08G 18/38* | (2006.01) |
| *C08G 18/40* | (2006.01) |
| *C08G 18/42* | (2006.01) |
| *C08G 101/00* | (2006.01) |

(52) U.S. Cl.
CPC ............ *C08J 9/146* (2013.01); *C08G 18/163* (2013.01); *C08G 18/1816* (2013.01); *C08G 18/225* (2013.01); *C08G 18/3806* (2013.01); *C08G 18/4018* (2013.01); *C08G 18/4211* (2013.01); *C08G 18/4213* (2013.01); *C08G 18/4829* (2013.01); *C08G 18/6633* (2013.01); *C08G 18/7671* (2013.01); *G01N 33/442* (2013.01); *C08G 2101/00* (2013.01); *C08G 2105/02* (2013.01); *C08J 2203/162* (2013.01); *C08J 2207/04* (2013.01); *C08J 2375/04* (2013.01)

(58) Field of Classification Search
CPC .............. C08G 18/163; C08G 18/1816; C08G 18/225; C08G 18/3806; C08G 18/4018; C08G 18/4211; C08G 18/4213; C08G 18/4829; C08G 18/6633; C08G 18/7671; C08G 2101/00; C08G 2105/02; C08J 9/146; C08J 2203/162; C08J 2207/04; C08J 2375/04; G01N 33/442
See application file for complete search history.

(56) References Cited

U.S. PATENT DOCUMENTS

| 4,595,711 | A | 6/1986 | Wood | |
|---|---|---|---|---|
| 5,789,458 | A | 8/1998 | Londrigan et al. | |
| 2011/0303867 | A1 | 12/2011 | Ling et al. | |
| 2012/0313035 | A1 | 12/2012 | Williams et al. | |
| 2013/0041048 | A1* | 2/2013 | Chen ................ | C08G 18/4018 516/12 |
| 2014/0100299 | A1 | 4/2014 | Taylor | |
| 2014/0162006 | A1 | 6/2014 | Albers et al. | |
| 2017/0313806 | A1 | 11/2017 | Yu et al. | |
| 2018/0079881 | A1 | 3/2018 | Zhang et al. | |
| 2018/0179358 | A1 | 6/2018 | Yu et al. | |

FOREIGN PATENT DOCUMENTS

CA 2615602 A1 6/2008

OTHER PUBLICATIONS

International Search Report with Written Opinion for PCT/US2016/012818 dated May 19, 2016.
International Search Report and Written Opinion of the International Searching Authority for International Patent Application No. PCT/US18/50070 dated Nov. 29, 2018 (7 pages).
International Search Report and Written Opinion for International Patent Application No. PCT/US18/50070 dated Nov. 29, 2018.
Two-Component Low Pressure Polyurethane Foam: An In-Depth Study of Shelf Life Stability with Hydrofluoroolefins, Megan Thomas, Ann Kelly-Rowley and Rachel Brooner, The Dow Chemical Company, copyright 2018 American Chemistry Council.

* cited by examiner

*Primary Examiner* — John M Cooney
(74) *Attorney, Agent, or Firm* — FisherBroyles, LLP; Louis F. Wagner, Esq.

(57) ABSTRACT

The invention described herein generally pertains to a composition and a method for improving the shelf life of a gaseous hydrofluoroolefin propellant, the improvement comprising at least the increased aromatic polyester polyol(s) in combination with a tertiary amine catalyst comprising at least two cyclohexyl rings and an aliphatic metal salt catalyst, the amine catalyst having less than 10% nitrogen on a weight basis.

13 Claims, 1 Drawing Sheet

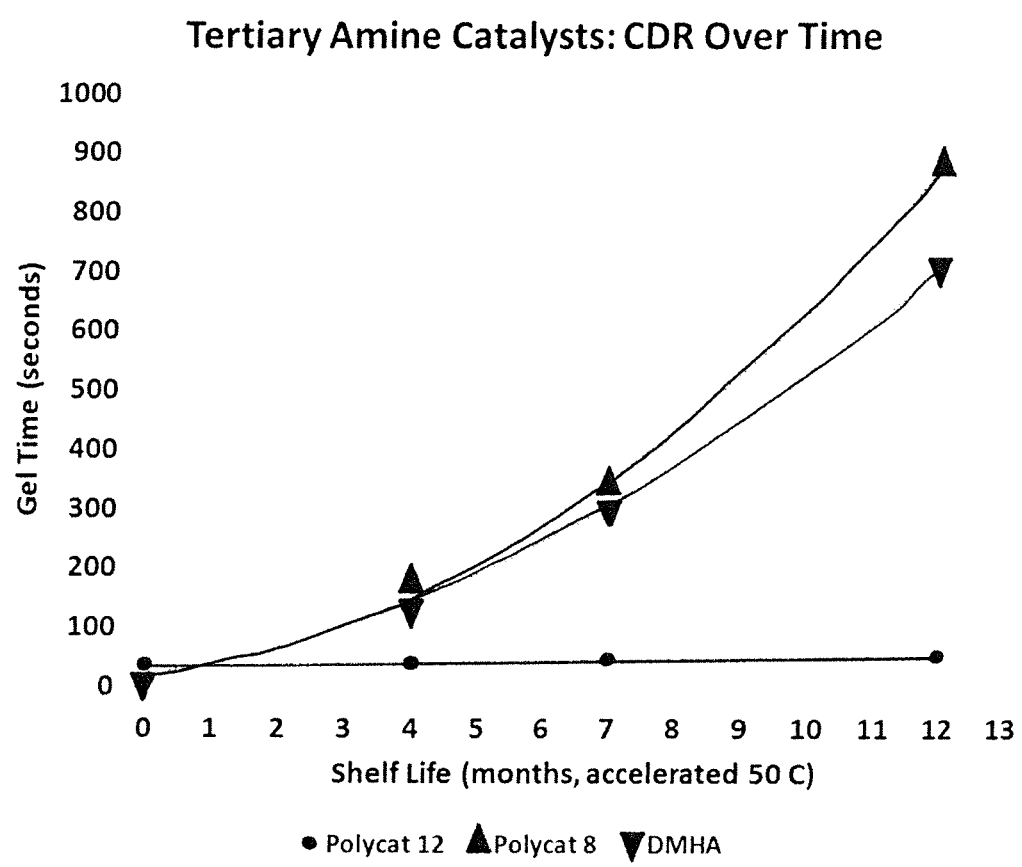

PROCESS FOR EXTENDING THE SHELF LIFE OF GASEOUS OLEFINIC PROPELLANTS IN POLYURETHANE FOAMS

CROSS-REFERENCE TO RELATED APPLICATIONS

The application is a divisional application of U.S. Ser. No. 14/992,338 filed 11 Jan. 2016 and claims priority to and fully incorporates by reference, patent application Ser. No. 62/102,289 filed on 12 Jan. 2015, both prior applications fully incorporated by reference.

TECHNICAL FIELD

The invention described herein pertains generally to extending the shelf life of gaseous olefinic propellants which are low in ozone depletion as well as global warming potential, and used in the preparation of polyurethane spray foams.

BACKGROUND OF THE INVENTION

The Significant New Alternatives Policy ("SNAP") Program of the United States Environmental Protection Agency ("EPA") is a program designed to evaluate and regulate substitutes for ozone-depleting chemicals that are being phased out under the stratospheric ozone protection provisions of the Clean Air Act ("CM").

The Montreal Protocol established a chlorofluorocarbon ("CFC") phase-out. It was known that CFCs had a high ozone depleting potential and a very high global warming potential. The next generation of propellants were hydrochlorofluorocarbon ("HCFC") compounds, which also were eventually phased out with a transition to hydrofluorocarbon ("HFC") compounds, which were known to be non-ozone depleting, but still have a high global warming potential. Through the Kyoto Protocol and implementing EU legislation and F-Gas regulation, HFC propellants are being phased out in an attempt to achieve compositions with low global warming potential and no ozone depletion effect. One of those replacements which has been identified through the above SNAP program is the olefinic gaseous propellant, trans-1-fluoro-3,3,3-trifluoroprop-1-ene (having a trade name of Solstice® GBA) and a Chemical Abstracts' Registry No. 29118-24-9. It has been identified by its manufacturer as a drop-in replacement for 1,1,1,2-tetrafluoroethane (having a trade name of Dymel® HFC-134a). HFC-134a has a global warming potential ("GWP") of ~1600, which is 1600 times the global warming effect of $CO_2$. Solstice® Gas Blowing Agent ("GBA") is a hydrofluoroolefin propellant ("HFO") and has an ozone depletion value of ~0 and a $GWP_{100}$ of <6. The atmospheric lifetime of Solstice® GBA is 14 days. The boiling point of Solstice® GBA is −19° C. (−3° F.).

This invention is particularly suited for extending the shelf life of the reactants used to synthesize polyurethane foams blown using the gaseous propellant, trans-1-fluoro-3,3,3-trifluoroprop-1-ene (having a trade name of Solstice® 1234ze or Solstice® GBA) in polyurethane foams.

Honeywell's Solstice® Gas Blowing Agent ("GBA") is nonflammable by ASTM E-681 and EU A11 test methods. It has a very low global warming potential ("GWP") of <1, a low Maximum Incremental Reactivity ("MIR"), Photochemical Ozone Creation Potential ("POCP") and is Volatile Organic Compound ("VOC") exempt.

As used in this application, a "two-component" froth foam means that one principal foam component is supplied in one pressurized container, typically the "A" container (i.e., polymeric isocyanate, fluorocarbons, etc.) while the other principal foam component is supplied in a second pressurized container, typically the "B" container (i.e., polyols, catalysts, flame retardants, fluorocarbons, etc.) recognizing that the designations "A" and "B" may be reversed in some other countries.

As also used in this application, "shelf life" means a polyurethane foam which when subjected to accelerated aging, still results in a foam having physical properties such as foam height, gel time, density, etc. within approximately 20% of those parameters prior to accelerated aging.

As further used in this application, "accelerated aging" means storing the reactant combination and propellant at 50° C. for 12-48 days prior to reacting the "A" and "B" cylinders and spraying the polyurethane foam. Using the Arrhenius equation, this equates to 3-12 months at room temperature.

As additionally used in this application, the term "approximately" or its equivalent symbol or "about" means a value within the acceptable norms of error measurement within the polyurethane foam industry, typically within about 10 percent of the stated value.

In a two-component polyurethane foam, the "A" and "B" components form the foam or froth, when they are mixed in the nozzle. Of course, chemical reactions with moisture in the air will also occur with a catalyst-containing two-component polyurethane foam after dispensing, but the principal reaction forming the polyurethane foam occurs when the "A" and "B" components are mixed, or contact one another in the dispensing nozzle. The dispensing apparatus for a two-component polyurethane foam application has to thus address not only the metering design concerns present in a one-component dispensing apparatus, but also the mixing requirements of a two-component polyurethane foam.

Further, a "frothing" characteristic of the foam (foam assumes consistency resembling shaving cream) is enhanced by the hydrofluoroolefin ("HFO") propellant (or similar) component, which is present in the "A" and "B" components. This HFO component is a compressed gas which exits in its liquid state under pressure and changes to its gaseous state when the liquid is dispensed into a lower pressure ambient environment, such as when the liquid components exit the gun and enter the nozzle.

While polyurethane foam is well known, the formulation varies considerably depending on application. In particular, while the polyols and isocyanates are typically kept separate in the "B" and "A" containers, other chemicals in the formulation may be placed in either container with the result that the weight or viscosity of the liquids in each container varies as well as the ratios at which the "A" and "B" components are to be mixed. In the dispensing gun applications which relate to this invention, the "A" and "B" formulations are such that the mixing ratios are generally kept equal so that the "A" and "B" containers are the same size. However, the weight, more importantly the viscosity, of the liquids in the containers invariably vary from one another. To adjust for viscosity variation between "A" and "B" chemical formulations, the "A" and "B" containers are charged (typically with an inert gas,) at different pressures to achieve equal flow rates. The metering valves in a two-component gun, therefore, have to meter different liquids at different pressures at a precise ratio under varying flow rates. For this reason (among others), some dispensing guns have a design where each metering rod/valve is separately adjustable against a separate spring to compensate not only for ratio variations in different formulations but also viscosity variations between the components. The typical two-component dispensing gun in use today can be viewed as two separate one-component dispensing guns in a common housing discharging their components into a mixing chamber or nozzle. In practice, often the gun operator adjusts the ratio settings to improve gun "performance" with poor results. To counteract this adverse result, the ratio adjustment then has to be "hidden" within the gun, or the design has to be such that the ratio setting is "fixed" in the gun for specific formulations. The gun cost is increased in either event and "fixing" the ratio setting to a specific formulation prevents interchangeability of the dispensing gun.

A still further characteristic distinguishing two-component from one-component gun designs, resides in the clogging tendencies of two-component guns. Because the foam foaming reaction commences when the "A" and "B" components contact one another, it is clear that, once the gun is used, the static mixer will clog with polyurethane foam or froth formed within the mixer. This is why the nozzles, which contain the static mixer, are designed as throw away items. In practice, the foam does not instantaneously form within the nozzle upon cessation of metering to the point where the nozzles have to be discarded. Some finite amount of time must elapse. This is a function of the formulation itself, the design of the static mixer and, all things being equal, the design of the nozzle.

The dispensing gun of the present invention is particularly suited for use in two-component polyurethane foam "kits" typically sold to the building or construction trade. Typically, a small kit contains two pressurized "A" and "B" cylinders of about 7.5 inches in diameter which are pressurized anywhere between 130-250 psi, a pair of hoses for connection to the cylinders and a dispensing gun, all of which are packaged in a container constructed to house and carry the components to the site where the foam is to be applied. When the chemicals in the "A" and "B" containers are depleted, the kit is sometimes discarded or the containers can be recycled. The dispensing gun may or may not be replaced. Since the dispensing gun is included in the kit, cost considerations dictate that the dispensing gun be relatively inexpensive. Typically, the dispensing gun is made from plastic with minimal usage of machined parts.

The dispensing guns cited and to which this invention relates are additionally characterized and distinguished from other types of multi-component dispensing guns in that they are typically, "airless" and often do not contain provisions for cleaning the gun. That is, a number of dispensing or metering guns or apparatus, particularly those used in high volume foam applications, are equipped or provided with a means or mechanism to introduce air or a solvent for cleaning or clearing the passages in the gun.

While the two-component dispensing guns discussed above function in a commercially acceptable manner, it is becoming increasingly clear as the number of in-situ applications for polyurethane foam increase, that the range or the ability of the dispensing gun to function for all such applications has to be improved. As a general example, the dispensing gun design has to be able to throttle or meter a fine bead of polyurethane froth in a sealant application where the kit is sold to seal spaces around window frames, door frames, and the like in the building trade. In contrast, where the kit is sold to form insulation, an ability to meter or flow a high volume flow of chemicals is required. Still yet, in an adhesive application, liquid spray patterns of various widths and thickness are required. While the "A" and "B" components for each of these applications are specially formulated and differ from one another, one dispensing gun for all such applications involving different formulations of the chemicals is needed.

In addition to all of the above issues, the switch from the propellant HFC-134a to the propellant HFO-1234ze has created yet another opportunity for the foam industry. While HFO-1234ze performs acceptably when initially formulated and dispensed from appropriate containers, the shelf life is quite limited, typically about 1 month. However, as is typical in this industry, the shelf life of 2-component cylinders is required to be 12 months or longer. Synthesized polyurethane foams using the propellant HFO-1234ze fail when the cylinders are stored for this period of time.

The industry requires a solution in which the newly approved hydrofluoroolefinic gaseous propellants have a longer shelf life before required usage.

SUMMARY OF THE INVENTION

In accordance with the present invention, there is provided a stable frothable two-component polyurethane foam, with a shelf life of at least 12 months using the HFO-1234ze propellant in both the "A" and "B" sides.

It is yet another aspect of the invention to provide a stable frothable two-component polyurethane foam having an increased aromatic polyester polyol content and no more than approximately 30% of aliphatic polyether polyols. This is counter-intuitive to industry thinking as illustrated below. In a more preferred aspect of the invention, the aliphatic polyether polyol content is no more than approximately 10%, and most preferably, the aliphatic polyether polyol content is approximately zero.

The above and other aspects of the invention are achieved by increasing the aromaticity of the polyol(s) used in the "B"-side formulation in combination with a catalyst package which comprises at least a mild tertiary amine catalyst (e.g., Polycat®-12) having at least two cyclohexyl rings in conjunction with a metal salt catalyst (e.g., potassium octoate) or 2,2 dimorpholinodiethylether (DMDEE).

What is described is a two-component polyurethane foam having a rise, a height, an initial foam gel time and a tack time which is within approximately 20% of those parameters using the propellant HFO-1234ze as compared to a polyurethane foam blown using the blowing agent HFC-134a after accelerated aging of said reactants when under pressure of at least approximately 130 psi, comprising:
   an "A-side" diisocyanate; and
   a "B-side" blend comprising:
   at least one aromatic polyester polyol and no more than approximately 10% aliphatic polyether polyol; and
   at least two catalysts comprising:
      at least one tertiary amine catalyst comprising at least two cyclohexyl rings;
      at least one aliphatic metal salt catalyst; and
   up to about 1.5 wt. % water.

In one aspect of the invention, the at least one aromatic polyester polyol is at least two aromatic polyester polyols. The polyurethane foam of claim 2 which further comprises no more than ~1% of an aliphatic polyether polyol.

In another aspect of the invention, the polyurethane foam will contain essentially no added water.

The polyurethane foam will preferably have at least one aromatic polyester polyol comprises at least two aromatic rings and the at least one tertiary amine catalyst comprises no more than 11 weight percent nitrogen, more preferably no more than 10 weight percent nitrogen.

At least one of the two catalysts for the polyurethane foam is an aliphatic metal salt, more specifically a metal alkanoate, and more specifically, a potassium alkanoate, namely potassium octoate.

A catalytic decay ratio of the gel time of the polyurethane foam exposed to accelerated aging involving storing the reactant combination and propellant at 50° C. for approximately 48 days prior to reacting the "A" and "B" cylinders and spraying the polyurethane foam increases approximately to no more than 2 for a polyurethane spray foam and approximately no more than 2.5 for a pour-in-place polyurethane foam.

In one aspect of the invention, the at least two aromatic polyester polyols are selected from the group consisting of:

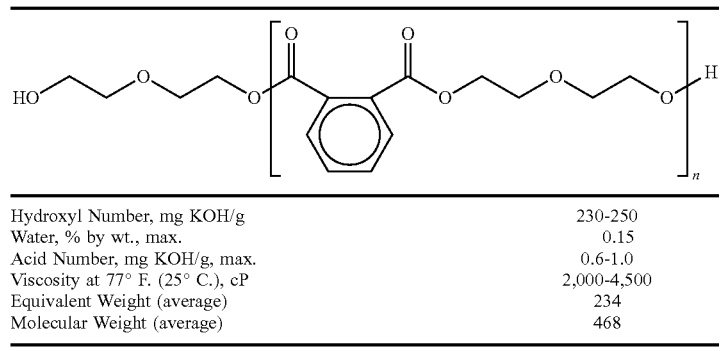

| | |
|---|---|
| Hydroxyl Number, mg KOH/g | 230-250 |
| Water, % by wt., max. | 0.15 |
| Acid Number, mg KOH/g, max. | 0.6-1.0 |
| Viscosity at 77° F. (25° C.), cP | 2,000-4,500 |
| Equivalent Weight (average) | 234 |
| Molecular Weight (average) | 468 | and

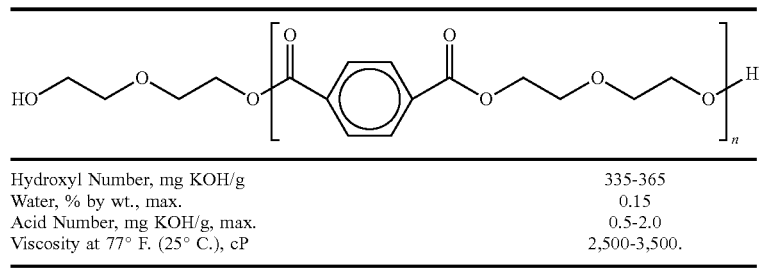

| | |
|---|---|
| Hydroxyl Number, mg KOH/g | 335-365 |
| Water, % by wt., max. | 0.15 |
| Acid Number, mg KOH/g, max. | 0.5-2.0 |
| Viscosity at 77° F. (25° C.), cP | 2,500-3,500. |

In another aspect of the invention, a process is described to improve the shelf life of gaseous HFO-blown two-component polyurethane foams comprising the steps of:
  using no less than 50% aromatic polyester polyols of all of the polyols used in the "B"-side formulation, said "B"-side formulation having no more than about 1.5% water by weight; and
  using a catalyst combination of a tertiary amine catalyst comprising at least two cyclohexyl rings, said tertiary amine catalyst having less than 11 weight percent nitrogen; and an aliphatic metal salt catalyst.

The tertiary amine catalyst has less than or equal to about 10% nitrogen on a weight basis and the "B"-side formulation having between 0.1-1.3% water by weight.

The tertiary amine catalyst has less than or equal to about 8% nitrogen on a weight basis and the "B"-side formulation having between 0.5-1.0% water by weight.

The polyurethane foam synthesized by the above process will comprise no more than approximately 10% aliphatic polyether polyol and more preferably, contain no added aliphatic polyether polyol.

In one aspect of the invention, the process further comprises the step of adding at least two aromatic polyester polyols.

A catalytic decay ratio of the gel time of the polyurethane foam exposed to accelerated aging involving storing the reactant combination and propellant at 50° C. for approximately 48 days prior to reacting the "A" and "B" cylinders and spraying the polyurethane foam increases approximately to no more than 2 for a polyurethane spray foam and approximately no more than 2.5 for a pour-in-place polyurethane foam.

The process employs accelerated testing in which the process of using a catalytic decay ratio of gel time of a polyurethane foam to determine the viability of said polyurethane foam, said process comprises the step of: calculating the catalytic decay ratio of the gel time of the polyurethane foam exposed to accelerated aging involving storing the reactant combination and propellant at 50° C. for approximately 48 days prior to reacting the "A" and "B" cylinders; and spraying the polyurethane foam; and measuring the catalytic decay ratio of the gel time; and determining if the increase is approximately no more than 2 for a polyurethane spray foam and approximately no more than 2.5 for a pour-in-place polyurethane foam.

These and other objects of this invention will be evident when viewed in light of the drawings, detailed description and appended claims.

BRIEF DESCRIPTION OF THE DRAWINGS

FIG. 1 is a plot of the catalytic decay ratio ("CDR") as a predictive prognosticator of polyurethane foam properties over time with various tertiary amine catalysts using the HFO-1234ze propellant.

DETAILED DESCRIPTION OF THE INVENTION

The best mode for carrying out the invention will now be described for the purposes of illustrating the best mode known to the applicant at the time of the filing of this patent application. The examples and figures are illustrative only and not meant to limit the invention, which is measured by the scope and spirit of the claims.

Currently, the only SNAP approved acceptable replacement for HFC-134a in low pressure spray polyurethane foams is the Honeywell Solstice® GBA blowing agent. This molecule presents significant technical challenges to a polyurethane foam chemist or formulator based on the inherent olefinic structure of the molecule, which was designed to break apart in the atmosphere.

The most significant challenge with the molecule is formulating a product that will meet the aggressive shelf life requirements of the low pressure spray polyurethane foam industry. Currently formulated products are pressurized into cylinders under a pressure of approximately 200-250 psi. The products are exposed to a large range of temperatures based on the end use application, and are delivered without the aid of proportioning units, etc.

Investigations to date prove degradation of the Solstice®1234ze propellant molecule and failure of the blown foam system when Solstice® 1234ze is used as a drop-in replacement for HFC-134a wherein only the propellant is substituted in the formulation.

While Solstice® 1234ze has desirable ODP and GWP characteristics, the propellant interacts with polyols and other additives in the "B"-side containers during prolonged storage (defined as greater than 3 months when using accelerated testing protocols, i.e., storage at 50° C. for 12 days) in ways which negatively impact the final characteristics of polyurethane foams in comparison to the same foams blown using conventional blowing agents such as HFC-134a. The sprayed two-component polyurethane foam fails with the olefinic propellant using standard polyurethane foam components as illustrated below.

TABLE I (Two-component PU foam composition using
HFO-1234ze propellant for HFC-134a)

| "B-side" Polyol | |
|---|---|
| aromatic polyester polyol having a functionality greater than or equal to 2.2 | 20-25% |
| sucrose polyether polyol based on a sucrose-glycerol mixture with a functionality of ~4.5 having a hydroxyl number of ~360 | 25-30% |
| glycerine-based oxypropylated polyether polyol having a functionality greater than or equal to 3 | 1-5% |
| brominated polyether with phthalate aromatic ring. | 2-15% |
| Flame Retardant/Plasticizer | |
| tris(2-chloropropyl) phosphate | 35-45% |
| Catalyst | |
| Polycat 5 - Tertiary amine | 1-5% |
| Potassium octoate | 1-5% |
| Surfactants | |
| Silicone surfactant | 0.5-1.5% |
| Non-silicone surfactant | 0.5-1.5% |
| Total (amounts adjusted to total 100%) | 100% |
| "A-side" | |
| Diisocyanate | 100% |

It should be noted that the propellant amounts were adjusted in "A" and "B" sides so as to compensate for viscosity differences and produce an approximately 1:1 dispensing ratio. Additionally, in addition to propellant gas, other inert gases may be included as is standard in the industry.

TABLE II (Typical two-component foam composition
using HFO-1234ze propellant)

| Analytical Results | Initial Sample Results after initial spraying | Aged Sample Result Results (after accelerated aging at 50° C. for 12 days) | Catalytic Decay Ratio ("CDR") Aged Gel (sec)/ Initial Gel (sec) |
|---|---|---|---|
| Gel time | 0:33 | 2:20 | 140/33 = 4.24 |
| Tack Time | 1:03 | 18:00+ | |

Over this short time period, the NFO-1234ze blown foam degrades and shows poor surface appearance as illustrated below using accelerated aging testing. By comparison, HFC-134a blown polyurethane foam looked essentially the same after the accelerated aging test. An acceptable CDR ratio would be approximately less than 2 for a spray foam and approximately less than 2.5 for a pour-in-place foam. As evidenced above, a CDR of 4.24 is unacceptable for either application. Therefore, what is quickly seen is that a compositional change in both the polyols used to synthesize the polyurethane foam coupled with a modification to the catalyst package.

Additional observations of the HFO-1234ze blown two-component blown polyurethane foam include poor cell structure, a decrease in the foam rise/height and a decrease in the closed cell content as shown below.

A breakdown in physical properties such as closed cell content, leads to further failures including decreased R-value/k-factor (thermal conductivity) and a decrease in performance as an air barrier. These are key performance characteristics for many applications in the industry. The foam blown from the aged cylinders showed little to no rise after it was applied. The surface showed that the blowing agent was boiling off. The foam was very soft for hours after, and still curing internally (sticky upon cut). The foam had very poor cell structure and general appearance.

Additional failures of note include an increase in density, which results in significantly decreased product yields, poor compression strength, tensile strength, etc. Another failure of note with the HFO-1234ze propellant is an incompatibility over the required shelf life with the flame retardant, tris(2-chloroisopropyl)phosphate ("TCPP"). TCPP is the most commonly used flame retardant and is required at loading levels of approximately 40% to meet the E84 class I requirement for SPF/building codes/etc. The systems tested using HFO-1234ze fail when levels exceed much over 20% loading when using a traditional polyether/polyester polyol blend in the "B"-side. This is problematic when attempting to achieve a class I rating and significantly limits the applications of the foam, unless reformulated in accord with the present invention.

Current generation propellant molecules like HFC-134a do not contain a carbon-carbon double bond. The new HFO-1234ze molecule contains a double bond as it is designed for degradation to maintain low global warming potential. This design was to address issues in Montreal and Kyoto protocols. This double bond is prone to attack by many other parts of the chemistry and will also degrade in pressurized systems currently used for polyurethane foams.

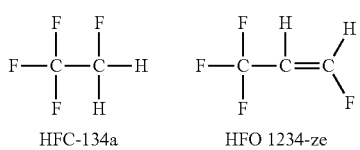

HFC-134a          HFO 1234-ze

At the present time, it appears that a high content of aromatic polyester polyol(s) aids in the shelf life of HFO-1234ze when in contact with typical "B"-side polyurethane foam reactants. While aliphatic polyether polyol(s) and/or aliphatic polyether polyol(s)/polyester polyol(s) blends are traditionally used in polyurethane foams blown using HFC-134a, (See Table I) formulations blown with HFO-1234ze require a counterintuitive switch to at least a majority amount of aromatic polyester polyols. An improved formulation using the blowing agent HFO-1234ze is as illustrated in Table Ill.

TABLE III (reformulated two-component foam composition using HFO-1234ze propellant)

| | Chemical | OH # | Wt. % |
|---|---|---|---|
| | "B-side" - 75 - 90% reactants/25 -10% propellant | | |
| | Polyol | | |
| 1st Polyol | Aromatic polyester polyol, f = 2.0 | 240 | 10-30 |
| 2nd Polyol | Branched, hydroxyl terminated, saturated, aromatic terephthalate polyester polyol, f = 2.2 | 350 | 20-50 |

TABLE III-continued (reformulated two-component foam composition using HFO-1234ze propellant)

| Chemical | OH # | Wt. % |
|---|---|---|
| Flame Retardant/Plasticizer | | |
| Tris (1-chloro-2-propyl) phosphate Flame Retardant | 0.1 | 20-45 |
| Tetrabromophthalate diol | 218 | 0-10 |
| Surfactant(s) | | |
| Polyether polydimethylsiloxane copolymer | 0 | 0.5-1.5 |
| Non-silicone organic surfactant | 36 | 0.5-1.5 |
| Catalyst | | |
| Potassium octoate/DEG (diethylene glycol) | 271 | 1-5 |
| Tertiary amine | 0 | 1-5 |
| Other | | |
| Water | | 0-1.5 |
| "A-side" - 94% MDI/6% propellant | | |
| p-MDI | | 100% |

In one aspect of the invention, two aromatic polyester polyols such PS 2352 & TB-350 are employed in the "B-side" formulation, i.e., Both have similar viscosities, hydroxyl numbers and acid values. The main difference between the components resides at least in part in the bonding to the benzene ring in which PS 2352 has the polymeric chain bonding through ortho positions on the ring while TB-350 has the polymeric chain bonding through the para positions on the ring.

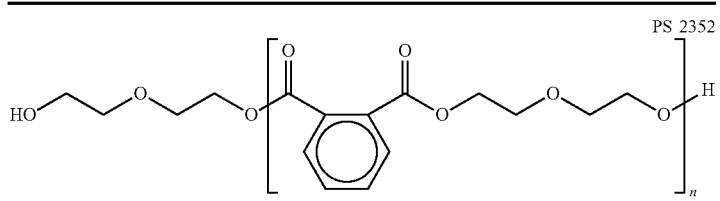

PS 2352

| Hydroxyl Number, mg KOH/g | 230-250 |
|---|---|
| Water, % by wt., max. | 0.15 |
| Acid Number, mg KOH/g, max. | 0.6-1.0 |
| Viscosity at 77° F. (25° C.), cP | 2,000-4,500 |
| Equivalent Weight (average) | 234 |
| Molecular Weight (average) | 468 |
| Color, Gardner | 4 |
| Density at 77° F. (25° C.), lb/U.S. gal | 9.9 |
| Specific Gravity at 77° F. (25° C.) | 1.19 |

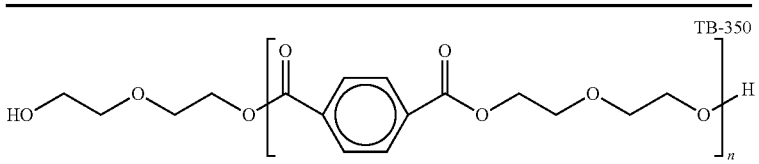

TB-350

| Hydroxyl Number, mg KOH/g | 335-365 |
|---|---|
| Water, % by wt., max. | 0.15 |
| Acid Number, mg KOH/g, max . | 0.5-2.0 |
| Viscosity at 77° F. (25° C.), cP | 2,500-3,500 |
| Color, Gardner | 4-5 |
| Specific Gravity at 77° F. (25° C.) | 1.233 |
| Functionality | 2.2 |

While two aromatic polyester polyols appear to be the preferred combination, it is believed, without being held to any one theory of operation or mechanism of action, that only one aromatic polyester polyol is required. Preliminary experimental results have shown that using 100% of the PS 2352 polyester, as well as 100% of the TB 350, produced acceptable polyurethane foams and the cured product looked good keeping the ratio of all other components the same. It is also believed that the incorporation of small amounts, e.g., less than approximately 30% of aliphatic polyether polyols will result in acceptable polyurethane foams, more preferably less than approximately 10% of aliphatic polyether polyols, and most preferably essentially no aliphatic polyether polyols.

Synthesized foams that were tested without the shielding of the benzene rings collapsed or fell apart at the end of three (3) month aging tests. Without the aromatic shielding attempts, all synthesized foams were unacceptable.

Associated analytical characteristics are tabularized in Table IV. As illustrated in the Table, all synthesized foams were within the limits of the catalytic decay ratio parameters of approximately 2 for a spray foam and approximately 2.5 for a pour-in-place foam (note the range of 1.0 to 1.28 below) using the accelerated aging testing protocol previously described.

TABLE IV

|  | Initial | 3 mo. | 6 mo. | 9 mo. | 12 mo. |
| --- | --- | --- | --- | --- | --- |
| Gel Time | 39 | 42 | 42 | 48 | 50 |
| Tack Free Time | 59 | 1:02 | 62 | 64 | 69 |
| Gx/Gi (CDR) | 1.0 | 1.077 | 1.077 | 1.230 | 1.282 |
| A/B Ratio | 1.08 | 1.08 | 1.16 | 1.15 | 1.16 |
| Surface | Good | Mediocre | Very Good | Good | Good |
| Interface | Very Good | Good | Good | Good | Good |
| Cell Structure | Very Good | Mediocre | Good | Good | Good |
| Dimensional Stability | Pass | Pass | Pass | Pass | Pass |

In order to determine the impact of changing from a polyether polyol to a polyester polyol system, a control experiment was performed in which the above polyester polyols of PS 2352 and TB 350 were tested in comparison to a system which used only polyether polyols typically used in the industry, namely Voranol 360 and Poly G 30-280. The experiment is summarized in Table V.

TABLE V (polyol study using HFO-1234ze propellant)

| "B-side"- 86% reactants/ 17% propellant | Chemical | Wt. % | Wt. % |
| --- | --- | --- | --- |

Polyester Polyol

PS 2352 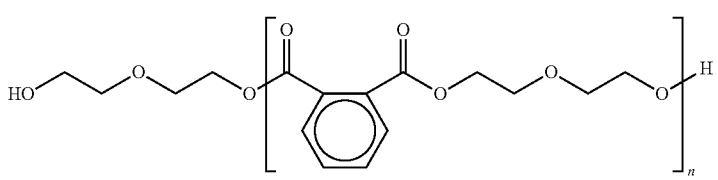 15.0

TB-350 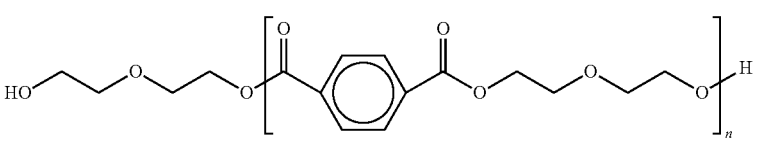 36.0

Polyether Polyol

Voranol 360 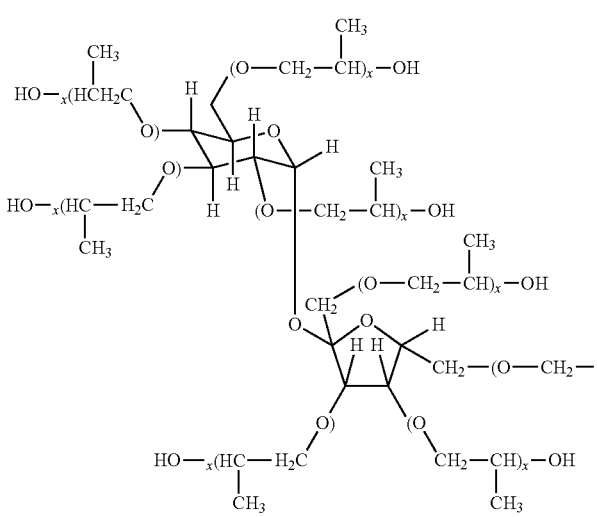 36.0

TABLE V-continued (polyol study using HFO-1234ze propellant)

| "B-side"- 86% reactants/ 17% propellant | Chemical | Wt. % | Wt. % |
|---|---|---|---|
| Poly G 30-280 | 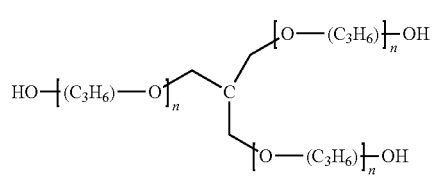 | 15.0 | |
| Flame Retardant/Plasticizer | | | |
| | Tris (1-chloro-2-propyl) phosphate | 36.6 | 41.6 |
| | Flame Retardant | | |
| | Tetrabromophthalate diol | 5.0 | |
| | Surfactant(s) | | |
| | Polyether polydimethylsiloxane copolymer | 1.0 | 1.0 |
| | Non-silicone organic surfactant | 1.0 | 1.0 |
| | Catalyst | | |
| | Potassium octoate/DEG (diethylene glycol) | 2.0 | 2.0 |
| | Polycat ®-12 | 2.5 | |
| | Other | | |
| | Water | 0.9 | 0.9 |
| "A-side"- 94% MDI/6% propellant | | | |
| | MDI | 100 | 100 |

As used above, Voranol 360 is a sucrose/glycerine (30/70) rigid polyether polyol having a nominal M.W. of ~610 and an average OH # of ~4.5. It is a multi-functional polyether polyol with high functionality (e.g. ~4.4-4.5) for dimensional stability. Poly G 30-280 is a polyether triol having a nominal M.W. of 30-280~600 and an average OH # (mg KOH/g) of ~274 and a maximum acid # of 0.05.

The above synthesized foams were tested using the accelerated testing protocol previously identified and summarized in Table VI.

TABLE VI

| | Initial | 3 mo. | 6 mo. | 9 mo. | 12 mo. |
|---|---|---|---|---|---|
| Polyester Polyol Results | | | | | |
| A/B | 1.08 | 1.08 | 1.16 | 1.15 | 1.16 |
| Gel Time (sec) | 39 | 42 | 42 | 48 | 50 |
| Tack Time (sec) | 59 | 62 | 62 | 64 | 69 |
| CDR | 1.00 | 1.08 | 1.08 | 1.23 | 1.28 |
| R value | 5.42 | 4.08 | 5.53 | 5.54 | 5.73 |
| % closed cell content | 96.34 | 44.20 | 82.45 | 94.74 | 80.81 |
| Polyether Polyol Results | | | | | |
| A/B | 0.96 | 0.98 | 0.90 | 0.92 | 0.91 |
| Gel Time (sec) | 124 | 146 | 169 | 295 | 320 |
| Tack Time (sec) | 161 | 355 | 568 | >1020 | 1412 |
| CDR | 1.00 | 1.18 | 1.36 | 2.38 | 2.58 |
| R value | 3.98 | — | — | — | — |
| % closed cell content | 61.10 | — | — | — | — |

As is easily seen, and quite counterintuitive in the industry, the polyester polyol combination was effective over the entire 12 months of accelerated aging studies, particularly as evidenced by the catalytic decay ratio, which at all times was below a threshold value of approximately less than 2 for a spray foam and approximately less than 2.5 for a pour-in-place foam using accelerated testing protocol. Further, the closed cell content and R-values were within acceptable values. This is contrasted to the polyether polyol combination, which did maintain a catalytic decay ratio of below the target values for 9 months of accelerated aging testing, but had unacceptable R-values and percentage of closed cell content. The cured foam collapse was so pronounced that samples sufficient for analysis could not be obtained.

Foam Catalyst System

In addition to the above sterically hindered aromatic polyester polyols, a non-conventional combination of catalysts is required. Polycat® 12 (a mild amine catalyst) possesses a significant amount of steric hindrance about the central nitrogen ("N") atom. That is not the case with Polycat® 5 (an aggressive amine catalyst) with three tertiary amines. At least one of the keys is the requirement that one of the catalysts include Dabco® K 15. A leading manufacturer of catalysts (Air Products) has characterized Polycat® 12 as a pour-in-place catalyst of medium potency. It is thought that having 0.9% water in the formula initiates the blowing reaction (R—NCO+$H_2O$=R—$NH_2$+$CO_2$), which generates a lot of heat for solvation of the Dabco® K-15 (potassium octoate) salt, making it active enough, early enough to provide a good synergistic total catalytic activity. It is thought that the high loading of Dabco® K-15 (potassium octoate) is also important to making Polycat® 12 work in an acceptable spray polyurethane foam formula. While Dabco® K-15 was effective in this application, other metal salts are believed to also be effective, including but not limited to Dabco® TMR 20, which is also a potassium-based catalyst.

What is indicated is that the catalysts and/or co-catalysts in the formulation must have a reduced percentage of nitrogen as illustrated in Table VII below. Preferably the percentage is below 10% nitrogen on a weight basis, more preferably below 7%.

TABLE VII

| Catalyst | M Wt. | pH | Nitrogen (#) | Nitrogen (%) | Name |
|---|---|---|---|---|---|
| Polycat ® 12 | 195.34 | 11.06 | 1 | 7.17 | Dicyclohexylmethyl amine |
| Polycat ® 8 | 127.23 | 11.77 | 1 | 11.01 | Dimethylcyclohexyl amine |
| DMDEE | 244.33 | 9.78 | 2 | 11.47 | Dimorpholinodiethyl ether |
| NEM | 115.18 | | 1 | 12.16 | N-Ethylmorpholine |
| NMM | 101.15 | | 1 | 13.85 | N-Methylmorpholine |
| Polycat ® 15 | 189.00 | 11.59 | 3 | 22.23 | Tetramethyldipropylene triamine |
| Polycat ® 5 | 173.30 | 11.05 | 3 | 24.25 | Pentamethyldiethyl triamine |
| DMP | 114.19 | | 2 | 24.53 | N,N'-DiMethylpiperazine |
| Dabco 33LV | 112.17 | 10.70 | 2 | 24.97 | Tetraethyl diamine |
| Dabco ® T | 146.23 | 11.05 | 2 | 19.16 | N,N,N'-trimethylaminoethyl ethanolamine |

Dabco ® K-15 (potassium octoate)/DEG (diethylene glycol)

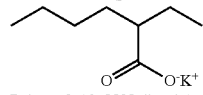

Polycat ® 12 (N,N-dicyclohexylmethylamine)

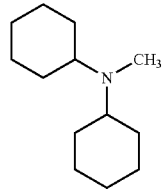

DMDEE (2,2'-dimorpholinodiethyl ether)

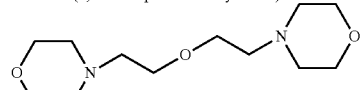

Polycat ® 5 (N,N,N',N',N''-pentamethyldiethylenetriamine)

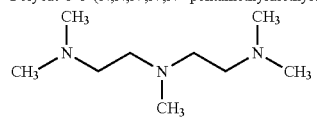

Polycat ® 8 (N,N-dimethylcyclohexylamine)

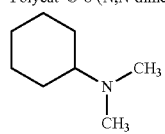

N,N-dimethylhexylamine

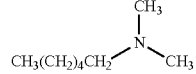

Without being bound to any one theory of operation or mechanism, it is believed that the increased presence of aromatic (e.g., benzene) rings in the polyols coupled with the increased steric hindrance attributable to the cyclohexyl rings in the amine catalysts in the "B"-side provides a high degree of steric hindrance to strong base/blowing agent interactions, while also serving to stabilize charge densities in polar polyurethane B-side formulas.

Without the benefit of the aromatic shielding, e.g., when using Polycat®-5 and Polycat®-8, the foam performance degraded significantly. This was proven in the following experiment.

TABLE VIII (catalyst study using HFO-1234ze propellant)

| "B-side"- 86% reactants/ 14% propellant | Chemical | Wt. % | Wt. % | Wt. % |
|---|---|---|---|---|
| | Polyol | | | |
| PS 2352 | [structure: HO-CH2CH2-O-CH2CH2-O-C(O)-C6H4-C(O)-O-CH2CH2-O-CH2CH2-O-]n H | 15.0 | 15.0 | 15.0 |
| TB-350 | [structure: HO-CH2CH2-O-CH2CH2-O-C(O)-C6H4-C(O)-O-CH2CH2-O-CH2CH2-O-]n H | 36.9 | 36.9 | 36.9 |
| | Flame Retardant/Plasticizer | | | |
| | Tris (1-chloro-2-propyl) phosphate Flame Retardant | 36.6 | 36.6 | 36.6 |
| | Tetrabromophthalate diol Surfactant(s) | 5.0 | 5.0 | 5.0 |
| | Polyether polydimethylsiloxane copolymer | 1.0 | 1.0 | 1.0 |
| | Non-silicone organic surfactant Catalyst | 1.0 | 1.0 | 1.0 |
| | Potassium octoate/DEG (diethylene glycol) | 2.0 | 2.0 | 2.0 |
| | Polycat ®-8 | | 1.63 | |
| | Polycat ®-12 | | | 2.5 |
| | N,N-dimethylhexylamine Other | 1.65 | | |
| | Water | 0.9 | 0.9 | 0.9 |
| | "A-side"- 93% MDI/7% propellant | | | |
| | MDI | 100 | 100 | 100 |

The above synthesized foams were tested using the accelerated testing protocol previously identified and summarized in Table IX.

TABLE IX

| | (accelerated months at 50° C.) | | | | |
|---|---|---|---|---|---|
| | Initial | 4 mo. | 7 mo. | 12 mo. | Gx/Gi (CDR) |
| Polycat ® -12 Gel Time (sec) | 32 | 39 | 45 | 50 | 1.56 |
| Polycat ® -8 Gel Time (sec) | 16 | 165 | 333 | 880 | 55 |
| DMHA Gel Time (sec) | 18 | 143 | 306 | | 17 |
| Polycat ® -12 Tack Time (sec) | 55 | 59 | 66 | 96 | 1.74 |
| Polycat ® -8 Tack Time (sec) | 27 | 487 | 495 | >1800 | 66 |
| DMHA Tack Time (sec) | 39 | 256 | 352 | | 9.0 |

Only the catalytic combination of a metal alkanoate with a mild tertiary amine catalyst with at least two aromatic rings in the moiety resulted in a stable system in which the catalytic decay ratio was within the satisfactory range of approximately less than 2 for a spray foam and approximately less than 2.5 for a pour-in-place foam using accelerated testing protocol as further illustrated in FIG. 1.

Plasticizer

While spray polyurethane foam formulations usually contain 30-40% of a plasticizer, the manufacturer, i.e., Honeywell, has shared that high levels of tris(1-chloro-2-propyl) phosphate ("TCPP")+Solstice® GBA is an undesirable combination for stability. However, this is not seen in the preferred combination when only aromatic polyester polyols are used.

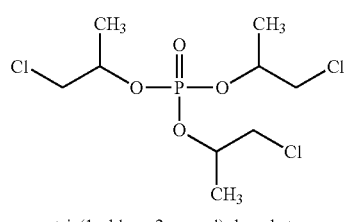

tris(1-chloro-2-propyl)phosphate

Flame Retardant (Tetrabromophthalate Diol)

A conventional flame retardant is often employed in the polyurethane composition, but is optional.

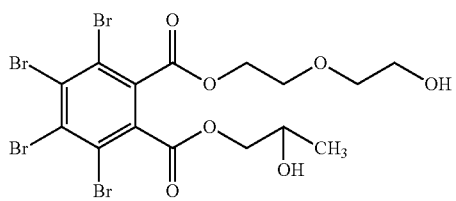 [SMILES: CC(O)COC(=O)c1c(Br)c(Br)c(Br)c(Br)c1C(=O)OCCOCCO]

Surfactant

A conventional combination of surfactants are employed at a weight percent of about 0.5-2%.

Tegostab® B-8433 Polyether polydimethylsiloxane copolymer foam stabilizer

Dabco® LK®-443 Non-silicone containing organic surfactant

Water Content

Water content also appears to play a role with the presence of higher amounts of water as a blowing agent (>1.5%) negatively impacting shelf life whereas low concentrations (<1.0%) of water are acceptable. Some structural applications however, require essentially no water, as shown in Table X.

The above synthesized foams were tested using the accelerated testing protocol previously identified and summarized in Table XI.

TABLE XI

| % H$_2$O | Gel Time | Density (pcf) | Compressive Strength (psi) | R-value | Closed Cell % |
|---|---|---|---|---|---|
| 0 | 26 | 3.28 | 48.64 | 5.3 | 78.8 |
| 0.9 | 33 | 2.34 | 32.35 | 5.1 | 81.9 |
| 2.0 | 40 | 1.83 | 22.12 | 5.1 | 76.6 |
| 3.0 | 48 | 1.57 | 11.64 | 4.3 | 82.5 |
| 4.0 | 52 | 1.45 | 9.64 | 4.2 | 81.4 |
| 5.0 | 56 | 1.27 | 6.42 | 4.0 | 42.4 |

For various applications, the synthesized foam will exhibit at least the following properties illustrated in Table XII.

TABLE X (water study using HFO-1234ze propellant with structural properties)

| "B-side"- 87% reactants/ 13% propellant Chemical | Wt. % | Wt. % | Wt. % | Wt. % | Wt. % | Wt. % |
|---|---|---|---|---|---|---|
| Polyol | | | | | | |
| PS 2352 | 20.0 | 20.0 | 20.0 | 20.0 | 20.0 | 20.0 |
| TB-350 | 32.5 | 32.5 | 32.5 | 32.5 | 32.5 | 32.5 |
| Flame Retardant/Plasticizer | | | | | | |
| Tris (1-chloro-2-propyl) phosphate | 4.0.0 | 39.1 | 38.0 | 37.0 | 36.0 | 35.0 |
| Flame Retardant | | | | | | |
| Tetrabromophthalate diol | | | | | | |
| Surfactant(s) | | | | | | |
| Polyether polydimethylsiloxane copolymer | 2.0 | 2.0 | 2.0 | 2.0 | 2.0 | 2.0 |
| Non-silicone organic surfactant | 1.0 | 1.0 | 1.0 | 1.0 | 1.0 | 1.0 |
| Catalyst | | | | | | |
| Potassium octoate/DEG (diethylene glycol) | 2.0 | 2.0 | 2.0 | 2.0 | 2.0 | 2.0 |
| Polycat ®-12 | 2.5 | 2.5 | 2.5 | 2.5 | 2.5 | 2.5 |
| Other | | | | | | |
| Water | 0 | 0.9 | 2.0 | 3.0 | 4.0 | 5.0 |
| "A-side"- 96.5-94.5% MDI/3.5-5.4% propellant | | | | | | |
| MDI | 100 | 100 | 100 | 100 | 100 | 100 |

TABLE XII

| | Pour-in-place or spray foam | Roof patch |
|---|---|---|
| R-value | 5-6 | |
| Compressive strength | 15 psi | >40 psi |
| Closed cell content | >90% | >90% |
| Gel time | <30 sec. | |
| Tack-free time | 30-60 sec. | |
| Dimensional stability | +/−5% of initial | +/−5% of initial |
| E-84 rating | A or B | Class-II |

Observations

Temperature appears to be a factor with storage at reduced temperatures extending shelf life.

What has been illustrated includes at least the following: high aromatic polyester polyol content, recognizing that polyether polyols possess little to no aromaticity. An SPF formula utilizing 100% aromatic polyester polyol content exhibits a shelf life of one year. The choice of flame retardant matters with flame retardants with higher aromatic content, e.g. PHT 4 diol, assisting. Those with lower aromaticity, e.g. TCPP, seem to further degrade shelf life when used in high concentrations. It is postulated (without being held to any one theory or mode of operation) that the increased presence of benzene rings in the B-side provides a high degree of steric hindrance to strong base/blowing agent interactions, while also serving to stabilize charge densities in polar polyurethane B-side formulas.

Currently, the only approved acceptable replacement for HFC-134a in the low pressure spray polyurethane foam industry is the Honeywell Solstice GBA blowing agent. This molecule presents significant technical challenges to a polyurethane foam chemist or formulator based on the inherent structure of the molecule, which was designed to break apart in the atmosphere.

The most significant challenge with the molecule is formulating a product that will meet the aggressive shelf life requirements of the low pressure spray polyurethane foam industry. Our products are pressurized into cylinders under a pressure of approximately 200-250 psi. The products are exposed to a large range of temperatures based on the end use application, and are delivered without the aid of proportioning units, etc.

The best mode for carrying out the invention has been described for purposes of illustrating the best mode known to the applicant at the time. The examples are illustrative only and not meant to limit the invention, as measured by the scope and merit of the claims. The invention has been described with reference to preferred and alternate embodiments. Obviously, modifications and alterations will occur to others upon the reading and understanding of the specification. It is intended to include all such modifications and alterations insofar as they come within the scope of the appended claims or the equivalents thereof.

What is claimed is:

1. A two-component polyurethane foam comprising a reaction product of:
    an "A-side" diisocyanate with an HFO-1234ze propellant; and
    a "B-side" blend with an HFO-1234ze propellant;
    the polyurethane foam reaction product comprising:
        at least two aromatic polyester polyols and no more than approximately 10 wt. % aliphatic polyether polyol,
    and wherein the at least two aromatic polyester polyols comprise:

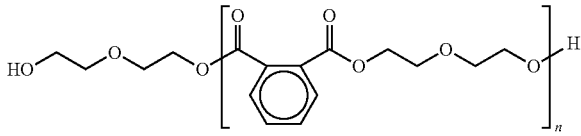

having a viscosity at 77° F. (25° C.), of between approximately 2,000-4,500 cP; and
    n being a value sufficient to achieve the viscosity; and

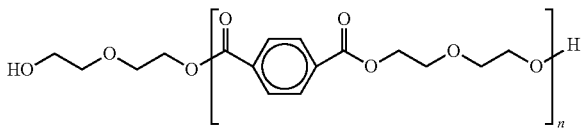

having a viscosity at 77° F. (25° C.) of between approximately 2,500-3,500 cP; and
    n being a value sufficient to achieve the viscosity;
    at least two catalysts comprising:
        at least one tertiary amine catalyst comprising at least two cyclohexyl rings;
        at least one aliphatic metal salt catalyst; and
    up to about 1.5 wt. % water.

2. The polyurethane foam of claim 1 which further comprises
    no more than ~1 wt. % of an aliphatic polyether polyol.

3. The polyurethane foam of claim 1 comprising:
    essentially no added water.

4. The polyurethane foam of claim 1 in which at least one of the at least two aromatic polyester polyols comprises:
    at least two aromatic rings.

5. The polyurethane foam of claim 1 wherein
    the at least one tertiary amine catalyst comprises no more than 11 wt. % nitrogen.

6. The polyurethane foam of claim 5 wherein
    the at least one tertiary amine catalyst comprises no more than 10 wt. % nitrogen.

7. The polyurethane foam of claim 1 wherein
    the aliphatic metal salt is a metal alkanoate.

8. The polyurethane foam of claim 7 wherein
    the metal alkanoate is a potassium alkanoate.

9. The polyurethane foam of claim 8 wherein
    the potassium alkanoate is potassium octoate.

10. The polyurethane foam of claim 1 which further comprises:
    a halogenated plasticizer.

11. The polyurethane foam of claim 10 which further comprises:
    a brominated phthalate diol flame retardant.

12. The polyurethane foam of claim 11 which further comprises:
    at least one surfactant.

13. The polyurethane foam of claim 12 in which the "A-side" and "B-side" further comprise:
    an inert pressurizing gas.

* * * * *